(12) United States Patent
Agu et al.

(10) Patent No.: US 10,539,549 B2
(45) Date of Patent: Jan. 21, 2020

(54) MOBILE BLOOD ALCOHOL CONTENT AND IMPAIRMENT SENSING DEVICE

(71) Applicant: WORCESTER POLYTECHNIC INSTITUTE, Worcester, MA (US)

(72) Inventors: Emmanuel Agu, Ashland, MA (US); Christina Aiello, Methuen, MA (US)

( * ) Notice: Subject to any disclaimer, the term of this patent is extended or adjusted under 35 U.S.C. 154(b) by 181 days.

(21) Appl. No.: 15/783,414

(22) Filed: Oct. 13, 2017

(65) Prior Publication Data

US 2018/0284100 A1 Oct. 4, 2018

Related U.S. Application Data

(60) Provisional application No. 62/407,791, filed on Oct. 13, 2016.

(51) Int. Cl.
*G01N 33/497* (2006.01)
*G01N 33/98* (2006.01)
*A61B 5/00* (2006.01)
*A61B 5/145* (2006.01)
*A61B 5/11* (2006.01)
*A61B 5/024* (2006.01)

(52) U.S. Cl.
CPC ......... *G01N 33/4972* (2013.01); *A61B 5/681* (2013.01); *G01N 33/98* (2013.01); *A61B 5/0008* (2013.01); *A61B 5/024* (2013.01); *A61B 5/02438* (2013.01); *A61B 5/112* (2013.01); *A61B 5/1118* (2013.01); *A61B 5/14546* (2013.01); *A61B 2562/0219* (2013.01)

(58) Field of Classification Search
CPC ............ A61B 2562/0219; A61B 5/024; A61B 5/02438; A61B 5/1118; A61B 5/112
See application file for complete search history.

(56) References Cited

U.S. PATENT DOCUMENTS

| | | | |
|---|---|---|---|
| 2008/0045804 A1* | 2/2008 | Williams | A61B 5/112 600/300 |
| 2011/0112443 A1* | 5/2011 | Williams | A61B 5/112 600/595 |
| 2011/0264010 A1* | 10/2011 | Williams | A61B 5/112 600/595 |

(Continued)

OTHER PUBLICATIONS

LaRose et al., "Smartphone Gait Inference", Worcester Polytechnic Institute, Apr. 2015. (Year: 2015).*

(Continued)

*Primary Examiner* — David A Rogers
(74) *Attorney, Agent, or Firm* — Duquette Law Group, LLC (57) ABSTRACT

In a mobile sensing device, a method of detecting blood alcohol content includes receiving time-series gait data from at least one sensor of the mobile sensing device as a user walks and detecting a set of attributes associated with the time-series gait data, each attribute of the set of attributes related to the user's gait. The method includes comparing the set of attributes with a machine learning classification model learned from a training data set of attributes to determine at least one of a blood alcohol content range of the user and an impairment level of the user and outputting a notification associated with the at least one of the blood alcohol content range of the user and the impairment level of the user.

17 Claims, 7 Drawing Sheets

(56) References Cited

U.S. PATENT DOCUMENTS

| | | | | |
|---|---|---|---|---|
| 2012/0218123 | A1* | 8/2012 | Ji | A61B 5/7232 |
| | | | | 340/870.07 |
| 2012/0330109 | A1* | 12/2012 | Tran | A61B 5/0022 |
| | | | | 600/301 |
| 2014/0128753 | A1* | 5/2014 | Luna | A61B 5/02438 |
| | | | | 600/500 |
| 2014/0235965 | A1* | 8/2014 | Tran | A61B 5/0006 |
| | | | | 600/301 |
| 2014/0305204 | A1* | 10/2014 | Hong | A63B 71/06 |
| | | | | 73/504.08 |
| 2015/0025393 | A1* | 1/2015 | Hong | A61B 5/02427 |
| | | | | 600/479 |
| 2015/0182130 | A1* | 7/2015 | Utter, II | A61B 5/0205 |
| | | | | 600/483 |
| 2016/0066820 | A1* | 3/2016 | Sales | A61B 5/1114 |
| | | | | 600/595 |
| 2016/0166180 | A1* | 6/2016 | Martin | A61B 5/112 |
| | | | | 702/141 |
| 2016/0287166 | A1* | 10/2016 | Tran | H04B 1/3827 |

OTHER PUBLICATIONS

Mohammed et al., "Recognition of gait cycle phases using wearable sensors", Robotics and Autonomous Systems, No. 75, 2016. (Year: 2016).*

Martinez et al., "Unsupervised Segmentation and Labeling for Smartphone Acquired Gait Data", (Year: 2016).*

* cited by examiner

MOBILE BLOOD ALCOHOL CONTENT AND IMPAIRMENT SENSING DEVICE

RELATED APPLICATIONS

This patent application claims the benefit of U.S. Provisional Application No. 62/407,791, filed on Oct. 13, 2016, entitled, "Blood Alcohol Content Sensing System," the contents and teachings of which are hereby incorporated by reference in their entirety.

BACKGROUND

Alcohol abuse is the third leading lifestyle-related cause of death for individuals in the United States, causing 88,000 deaths each year in the United States from 2006-2010. To limit the physical and mental harm caused by alcohol abuse, a variety of devices are used to provide varying levels of intoxication detection.

For example, the SCRAM Continuous Alcohol Monitoring device is an ankle-worn, commercial detection device. It is typically used for high-risk, Driving Under the Influence (DUI) alcohol offenders who have been ordered by a court not to consume alcohol. The SCRAM device samples the wearer's perspiration once every 30 minutes in order to measure his BAC levels. In another example, the Kisai Intoxicated LCD Watch, as produced by TokyoFlash, Japan, is a watch that includes a built-in breathalyzer. By breathing into its breathalyzer, the watch detects and displays graphs of the user's blood alcohol content (BAC) level.

Additionally, machine learning approaches to detect BAC from data gathered from conventional smartwatches have been used. As smartwatches have been developed, attempts have been made to utilize them to detect alcohol consumption levels. For example, certain conventional approaches have estimated a user's intoxication level using heart rate and temperature detected by a smartwatch worn by the user.

Further, certain smartphone applications, such as Intoxicheck (http://intoxicheck.appstor.io) can detect alcohol impairment in users. In use, a user takes a series of reaction, judgment, and memory challenges before and after drinking, which are compared to estimate their intoxication level. Other smartphone applications detect intoxication detection from gait. For example, certain conventional smartphone applications relate to a passive phone-based system that use the smartphone's accelerometer data to detect whether users had consumed alcohol or not.

SUMMARY

Previous devices and approaches suffer from a variety of deficiencies. For example, certain conventional devices require a user to actively engage the device in order to determine the user's relative sobriety. For instance, the Intoxicheck smartphone application requires the user to takes a series of reaction, judgment, and memory challenges after drinking to estimate their intoxication level. Further, the Kisai Intoxicated LCD Watch requires the user to blow into a built-in breathalyzer in order to detect and display the user's BAC level. In either case, both Intoxicheck and the Kisai Intoxicated LCD Watch require active user engagement, which may deter adoption and reduce their scalabilities.

In another example, certain intoxication detection devices, such as the SCRAM device and the Kisai Intoxicated LCD watch, are dedicated, stand-alone devices. Therefore, a user must purchase and use these device separate from other conventional day-to-day devices that he may use, such as a smartphone or smartwatch. This may also deter adoption and reduce their scalabilities.

The use of conventional mobile devices to detect a user's BAC also suffer from a variety of deficiencies. For example, certain mobile devices can utilize machine learning approaches to detect BAC solely from user heart rate and temperature data. However, these conventional approaches do not utilize user gait information which, aside from the direct breathalyzer test, is a highly reliable indicator of human intoxication. In another example, certain smartphone applications relate to a passive system that use only the smartphone's accelerometer data to detect whether or not a user has consumed alcohol. However, these applications do not utilize either postural sway features extracted from gyroscope data or normalization to account for different walking styles and can lead to an unusable level of BAC accuracy.

By contrast to conventional devices and approaches, embodiments of the present innovation relate to a mobile blood alcohol content and impairment sensing device. In one arrangement, the mobile sensing device, such as a smartphone, includes a set of sensors, such as an accelerometer and gyroscope. During operation, the mobile sensing device receives accelerometer and gyroscope sensor data generated as a user walks. The mobile sensing device then utilizes a machine learning approach to classify the user's gait attributes, as derived from the sensor data, as being indicative of a certain BAC or level of impairment. With such an approach, the mobile sensing device is configured to operate passively to determine the user's level of intoxication or impairment.

In one arrangement, embodiments of the innovation relate to a mobile sensing device, having at least one sensor and a controller having a processor and a memory, the controller disposed in electrical communication with the at least one sensor. The controller is configured to receive time-series gait data from at least one sensor of the mobile sensing device as a user walks; detect a set of attributes associated with the time-series gait data, each attribute of the set of attributes related to the user's gait; compare the set of attributes with a machine learning classification model learned from a training data set of attributes to determine at least one of a blood alcohol content range of the user and an impairment level of the user; and output a notification associated with the at least one of the blood alcohol content range of the user and the impairment level of the user.

In one arrangement, in a mobile sensing device, embodiments of the innovation relate to a method of detecting blood alcohol content which includes receiving time-series gait data from at least one sensor of the mobile sensing device as a user walks and detecting a set of attributes associated with the time-series gait data, each attribute of the set of attributes related to the user's gait. The method includes comparing the set of attributes with a machine learning classification model learned from a training data set of attributes to determine at least one of a blood alcohol content range of the user and an impairment level of the user and outputting a notification associated with the at least one of the blood alcohol content range of the user and the impairment level of the user.

BRIEF DESCRIPTION OF THE DRAWINGS

The foregoing and other objects, features and advantages will be apparent from the following description of particular embodiments of the innovation, as illustrated in the accompanying drawings in which like reference characters refer to the same parts throughout the different views. The drawings are not necessarily to scale, emphasis instead being placed upon illustrating the principles of various embodiments of the innovation.

DETAILED DESCRIPTION

Embodiments of the present innovation relate to a mobile blood alcohol content and impairment sensing device. In one arrangement, the mobile sensing device, such as a smartphone, includes a set of sensors, such as an accelerometer and gyroscope. During operation, the mobile sensing device receives accelerometer and gyroscope sensor data generated as a user walks. The mobile sensing device then utilizes a machine learning approach to classify the user's gait attributes, as derived from the sensor data, as being indicative of a certain BAC or level of impairment. With such an approach, the mobile sensing device is configured to operate passively to determine the user's level of intoxication or impairment.

Figure 1:
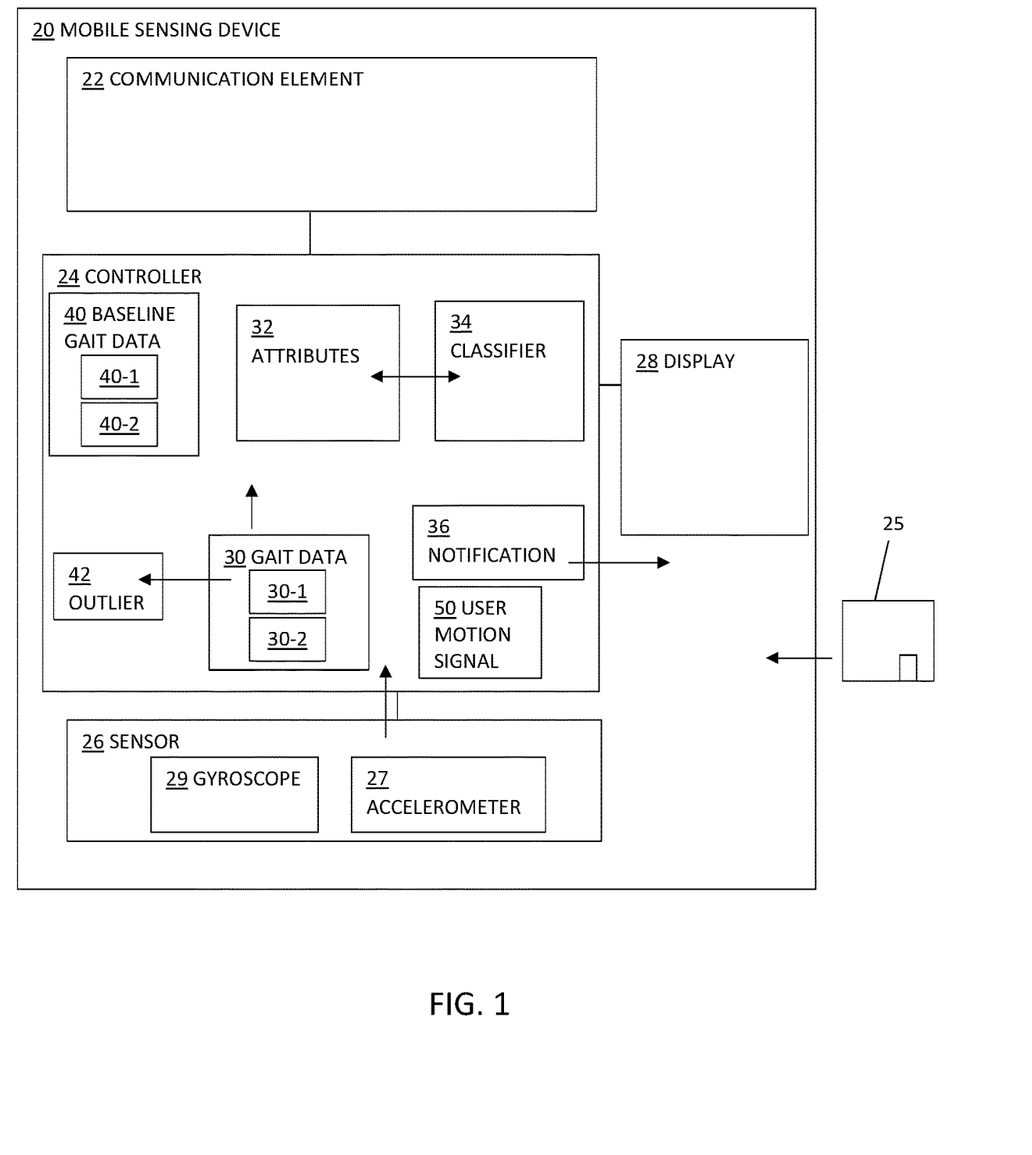
FIG. 1 illustrates a schematic representation of a mobile sensing device, according to one arrangement.

FIG. 1 illustrates a schematic representation of an example of a mobile sensing device 20. While the mobile sensing device 20 can be configured as a variety of types of devices, in one arrangement the mobile sensing device 20 is configured as a computerized device, such as a mobile phone (e.g., smartphone), mobile watch (e.g., smartwatch), a tablet device, a laptop computer, or other computerized device. In the case where the mobile sensing device 20 is configured as a smartphone, the mobile sensing device 20 includes a communication element 22 such as a transmitter, a receiver, a microphone, and a speaker configured to allow a user to communicate with other mobile devices. The mobile sensing device 20 also includes a controller 24, such as a memory and a processor, disposed in electrical communication with the communication element 22, with one or more sensors 26, such as an accelerometer and a gyroscope, and with a display 28, such as a touch screen display.

In one arrangement, the controller 24 of the mobile sensing device 20 is configured to detect a user's blood alcohol content and/or impairment level based upon time-series gait data received from the sensors 26 as a user walks. For example, as will be described in detail below, the mobile sensing device 20 is configured to collect time-series gait data signals from the accelerometer 27 and gyroscope 29 and derive attributes of the user's gait based upon these raw accelerometer and gyroscope data signals. Further, the mobile sensing device 20 is configured to classify the attributes into blood alcohol content (BAC) ranges and/or impairment levels and to provide an output regarding the user's detected BAC and/or impairment levels.

In one arrangement, the controller 24 of the mobile sensing device 20 can store an application for detecting a BAC or impairment level of a user based upon input from the sensors 26. The detection application installs on the controller 24 from a computer program product 25. In some arrangements, the computer program product 25 is available in a standard off-the-shelf form such as a shrink wrap package (e.g., CD-ROMs, diskettes, tapes, etc.). In other arrangements, the computer program product 25 is available in a different form, such downloadable online media. When performed on the controller 24 of the mobile sensing device 20, the detection application causes the mobile sensing device 20 to detect the BAC range or impairment level of a user and to provide an output or notification 36 regarding the detected range or level.

In one arrangement, when the detection application installs on the controller 24 from a computer program product 25, the controller 24 is configured to launch and execute the application in the background of the mobile sensing device 20. Such background execution does not require the user to either initiate or interact with the detection application or with the mobile sensing device 20. By executing the application in the background, the mobile sensing device 20 is configured to operate as a passive device. That is, the mobile sensing device 20 can detect the BAC range or impairment level of the user with minimal, if any, active input from the user. With such a configuration, the detection application can be adopted and utilized by users without requiring the user's active participation with the mobile sensing device 20.

With continued reference to FIG. 1, and as provided above, conventional mobile sensing device 20, such as smartphones, typically include an accelerometer 27 and a gyroscope 29. Each of these devices 27, 29 is configured to generate a time-series gait data signal 30, hereinafter referred to as time-series gait data 30, that can identify either a user's BAC range in the case of alcohol intoxication or level of impairment in the case of non-alcohol based intoxication, such as by opioids or other drugs.

In one arrangement, the accelerometer 27 is configured to generate time-series gait data 30-1 which identifies attributes associated with the user's walking pattern. For example, the time-series gait data 30-1 from the accelerometer 27 can identify, among a number of attributes, the cadence and the symmetry of the user's walking pattern. Variations in these attributes relative to a classifier such as a machine learning classification model 34 learned from a training data set of attributes 35 can relate to the user having a BAC or impairment level in a particular, elevated range.

In one arrangement, the gyroscope 29 is configured to provide time-series gait data 30-2 that can identify a user's sway area along a YZ (anterior-posterior) plane, an XY (mediolateral) plane, or an XZ (rotational) plane. Increases in the user's physical sway area relative to the machine learning classification model 34 learned from the training data set of attributes 35 can relate to the user having a BAC or impairment level in a particular, elevated range.

The mobile sensing device 20 can be configured to detect user BAC ranges or impairment levels in a variety of ways.

The following provides a description of an example of the operation of the mobile sensing device 20, according to one arrangement.

During operation, once the user has installed the detection application on the mobile sensing device 20, the user initially configures or trains the mobile sensing device 20 to recognize a baseline gait data signal 40 while the user is sober. For example, during a configuration process, as the user walks while sober, the mobile sensing device 20 collects baseline accelerometer gait data 40-1 from the accelerometer 27 and baseline gyroscope gait data 40-2 from the gyroscope 29. The mobile sensing device 20 stores the baseline gait data signal 40 as a basis for comparison against future time-series gait data 30 collected by the mobile sensing device 20, as will be discussed below.

As provided above, once installed, the mobile sensing device 20 is configured to execute the detection application in the background, such that the mobile sensing device 20 can detect the BAC range or impairment level of the user with minimal, if any, user-input. When the mobile sensing device 20 executes the detection application in a substantially continuous manner, the mobile sensing device 20 can receive motion data 50 from the sensors 26 in substantially periodic intervals or as the user moves (e.g., sits, stands, runs, jumps, etc.). However, the mobile sensing device 20 is configured to collect and store time-series gait data 30 from the sensors during times of interest, such as when the user is walking. Accordingly, during operation and prior to collecting the time-series gait data 30, the mobile sensing device 20 is configured to detect if the user is walking based upon the motion data 50 received.

Figure 2:
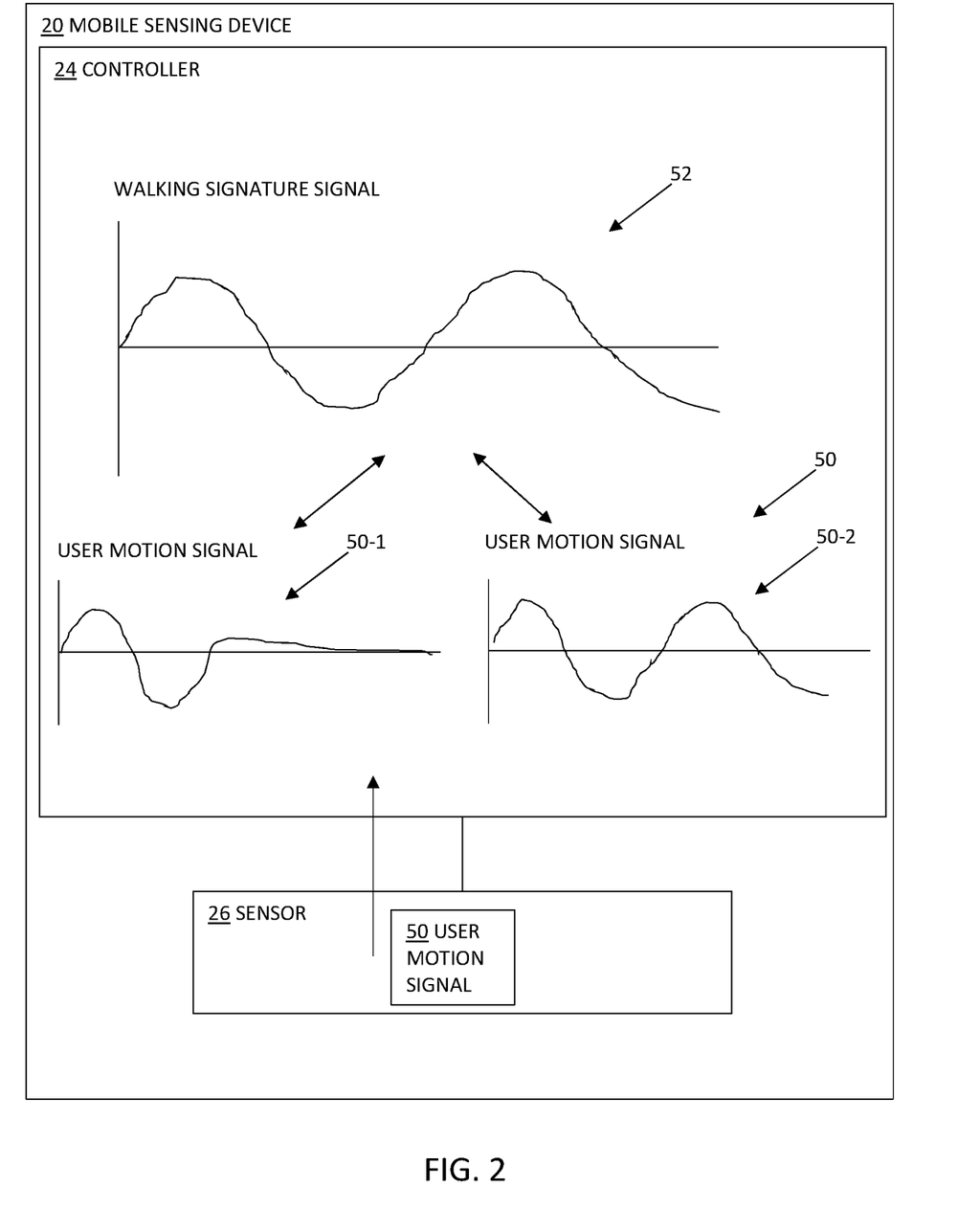
FIG. 2 illustrates a schematic representation of the mobile sensing device of FIG. 1 configured to detect a user's motion as walking motion, according to one arrangement.

In one arrangement, with reference to FIG. 2, the controller 24 of the mobile sensing device 20 is configured to receive user motion signals 50 from the sensors 26 at periodic intervals, such as at a rate of once every one to five minutes. During operation, the mobile sensing device 20 compares the user motion signals 50 with a walking signature signal 52 which is stored by the mobile sensing device's controller 24 and identifies some aspect of the user's gait, such as cadence, as the user walks. When the mobile sensing device 20 detects the user motion signal 50 as substantially corresponding to the walking signature signal 52, the mobile sensing device 20 can identify the user motion signal 50 as indicating that the user is in the process of walking.

For example, assume the case where the mobile sensing device 20 receives, at a first time, a first user motion signal 50-1 from the accelerometer 27. Based on a comparison between the first user motion signal 50-1 and the walking signature signal 52 stored by the controller 24, the mobile sensing device 20 can identify a substantial difference between the signals 50-1, 52 to identify the user motion signal 50-1 as not indicating that the user is in the process of walking. For example, the substantial difference can include a difference in the accelerometer and gyroscope peak values between the user motion signal 50-1 and the walking signature signal 52 and/or a difference in the signal strength between the user motion signal 50-1 and the walking signature signal 52. However, assume the case where the mobile sensing device 20 receives, at a second time, a second user motion signal 50-2 from the accelerometer 27. Based on a comparison between the second user motion signal 50-2 and the walking signature signal 52, the mobile sensing device 20 can identify a substantial similarity between the signals 50-2, 52 to identify the user motion signal 50-2 indicating that the user is in the process of walking. For example, the substantial similarity can include similar shapes and patterns of the user motion signal 50-1 and the walking signature signal 52 within a preconfigured tolerance range (e.g., +/−10%).

Returning to FIG. 1, in the case where the mobile sensing device 20 identifies the user motion signal 50 as corresponding to the walking signature signal 52, the mobile sensing device 20 is configured to then receive time-series gait data 30 from the sensors 26 of the mobile sensing device 20 as the user walks. In one arrangement, with reference to FIG. 3, the controller 24 can receive accelerometer time-series gait data 30-1 from the accelerometer 27 and can receive gyroscope time-series gait data 30-2 from the gyroscope 29 from both of the sensors 27, 29 in a substantially simultaneous manner. As provided above, the accelerometer time-series gait data 30-1 identifies attributes associated with a user's walking pattern while the gyroscope time-series gait data 30-2 can identify attributes associated with the user's sway area. Taken together, the time-series gait data 30-1, 30-2 allows the mobile sensing device 20 to provide a relatively robust assessment as to the user's BAC range or impairment level. However, the controller 24 can receive the time-series gait data 30 from only either of the accelerometer 27 or the gyroscope 29 and can use the respective data 30-1 or 30-2 to determine the BAC range or impairment level of the user.

Figure 3:
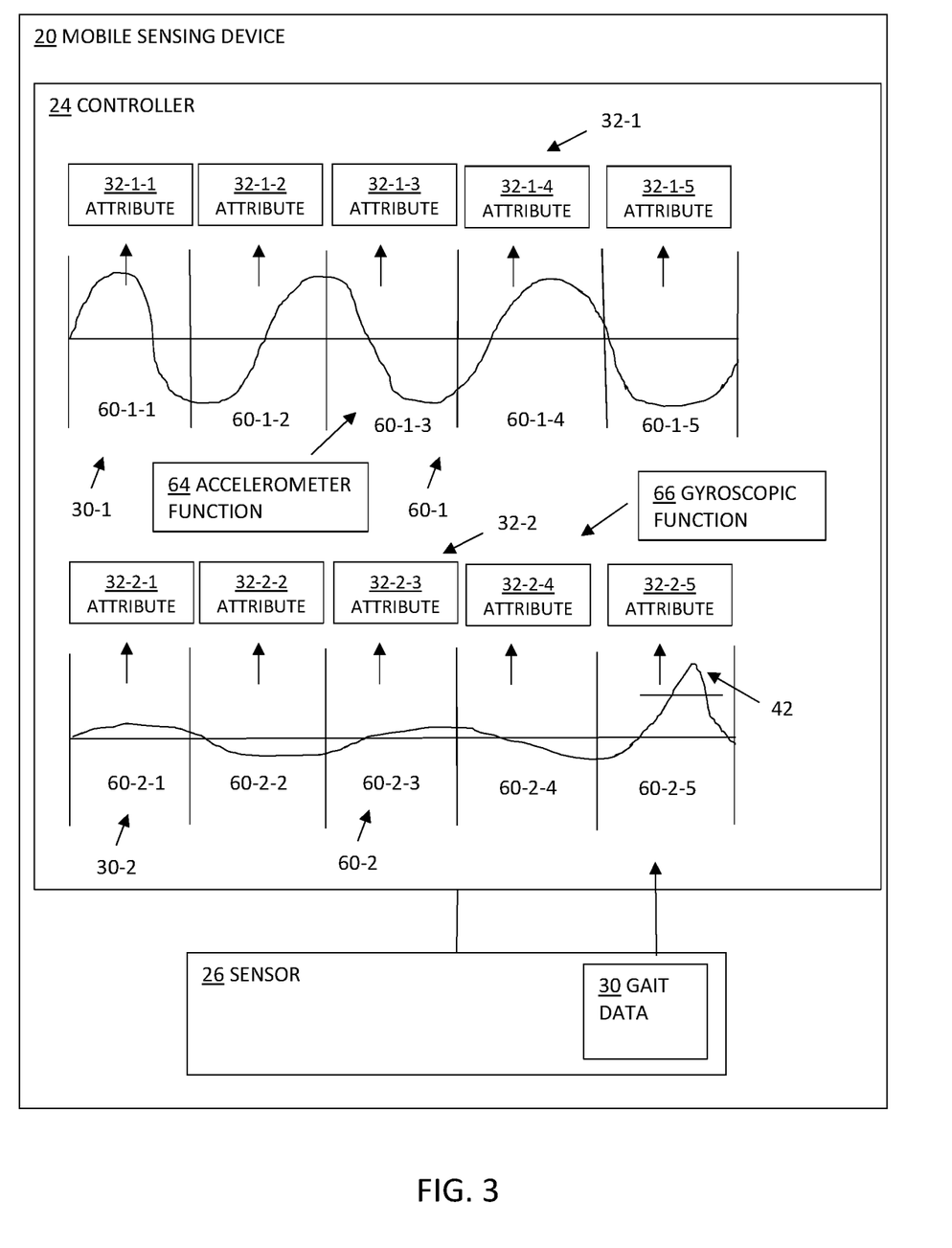
FIG. 3 illustrates a schematic representation of the mobile sensing device of FIG. 1 configured to detect a set of attributes associated with time-series gait data, according to one arrangement.

As the mobile sensing device 20 receives the time-series gait data 30, the controller 24 is configured to collect and store a sample of the time-series gait data 30 received. For example, the controller 24 is configured to store a thirty-second sample of the time-series gait data 30, as received from the sensor 26.

In one arrangement, once the controller 24 has received the time-series gait data 30, the controller 24 is configured to preprocess the time-series gait data 30 prior to analyzing the time-series gait data 30. In one arrangement, with reference to FIG. 3, as part of the preprocessing, the mobile sensing device 20 is configured to divide the time-series gait data 30 into gait data segments 60. For example, the controller 24 is configured to break the continuous time series data 30-1, 30-2 received from each of the accelerometer 27 and gyroscope 29, respectively, into five-second segments 60-1, 60-2 on which computations can then be performed. By segmenting the time series gait data 30-1, 30-2 into gait data segments 60, the controller 24 breaks the time-series gait data 30 into relatively smaller chunks to address the relatively rapid changes in the data within the sample of the time-series gait data 30.

Further, as part of the preprocessing, the mobile sensing device 20 is configured to identify and remove outlier values 42 from the time-series gait data 30. For example, as the user walks and as the mobile sensing device 20 collects time-series gait data 30, the user may generate anomalous gait data that is outside of the range typically generated during walking, such as if the user were to trip or fall while walking. To limit the effect of extreme or outlier gyroscope and accelerometer data time series gait data values on the analysis, the mobile sensing device 20 is configured to sort the accelerometer and gyroscope time series gait data 30-1, 30-2 and to remove outlier values 42, such as the top and bottom 1 percent of the time-series gait data 30 values.

For example, with reference to FIG. 3, the gyroscope time series gait data 30-2, the controller 24 can apply a sorting algorithm to the time series gait data 30-2 and, based upon the sorting, can identify the data of segment 60-2-5 as including outlier values 42, such as values that are at the top 1 percent of the values for the time series gait data 30-2. With such identification, the controller 24 is configured to remove these values from the segment 60-2-5 prior to further processing the gyroscope time series gait data 30-2.

Next, returning to FIG. 1, the mobile sensing device 20 is configured to detect a set of attributes 32 associated with the time-series gait data 30 where each attribute of the set of attributes 32 relates to the user's gait. In one arrangement, with reference to FIG. 3, in the case where the controller 24 has performed a preprocessing of the time-series gait data 30, the mobile device 20 is configured to extract the set of attributes 32 associated with each gait data segment 60 of the time-series gait data 30. For example, in the example illustrated, the mobile sensing device 20 extracts the attributes 32-1 of the accelerometer time series gait data 30-1 for each of segments 60-1-1 through 60-1-5 and detects the gyroscope time series gait data 30-2 for each of segments 60-2-1 through 60-2-5.

While the mobile sensing device 20 can detect the set of attributes 32 in a variety of ways, in one arrangement, the controller 24 is configured to apply particular functions to the time-series gait data 30 based upon the sensor utilized to collect the time-series gait data 30.

For example, in the case where the time-series gait data 30 is accelerometer time-series gait data 30-1, the controller 24 is configured to apply one or more accelerometer functions 64 to each of the gait data segments 60-1 to extract corresponding accelerometer attributes 32-1. In one arrangement, the accelerometer function 64 can be configured to extract an attribute 32-1 which relates to any of a number of steps taken, a cadence, a symmetry of a walking pattern, a kurtosis, an average gait velocity, a residual step length, a harmonic ratio of high and low frequencies, a residual step time, bandpower, signal to noise ratio, or a total harmonic distortion from each of the gait data segments 60-1 associated with the time-series gait data 30-1.

Table 1 provided below outlines eleven (11) attributes 32-1 that can be extracted from the accelerometer time-series gait data 30-1 by the corresponding accelerometer functions 64. It is noted that the listing of attributes 32 provided in Table 1 is by way of example only. It should be understood that additional attributes 32-1 can be extracted from the accelerometer time-series gait data 30-1 as well.

TABLE 1

| Attribute 32-1 | Attribute Description | Accelerometer Function 64 |
|---|---|---|
| Steps | Number of steps taken | calculation of signal peaks above one standard deviation away from mean of gravity corrected magnitude of signal |
| Cadence | Number of steps taken per minute | cadence = # of steps/minute |
| Skew | Lack of symmetry in one's walking pattern | $\text{skewness} = \dfrac{\frac{1}{n}\sum (x_i - \mu_x)^3}{\left[\frac{1}{n}\sum (x_i - \mu_x)^2\right]^{3/2}}$ <br><br> Where $x_i$ is the data sequence and $u_x$ is the average of all $x_i$ |
| Kurtosis | Measure of how outlier-prone a distribution is | $\text{kurtosis} = \dfrac{\frac{1}{n}\sum (x_i - \mu_x)^4}{\left[\frac{1}{n}\sum (x_i - \mu_x)^2\right]^2}$ <br><br> Where $x_i$ is the data sequence and $u_x$ is the average of all $x_i$ |
| Average gait velocity | Average steps per second divided by average step length | average gait velocity = [(average steps/sec)]/step length |
| Residual step length | Difference from the average in the length of each step | residual step length = distance/# of steps |
| Ratio | Ratio of high and low frequencies | $\text{harmonic ratio} = \dfrac{\sum_{i=1,3,5,\ldots} V_i}{\sum_{j=2,4,6,\ldots} V_j}$ <br><br> Where $V_i$ is the amplitude of odd-ordered harmonic frequency and $V_j$ is the even-ordered harmonic frequency |
| Residual step time | Difference in the time of each step | $\text{residual step time} = \dfrac{\sqrt{\frac{1}{n}\sum (\text{interval}_i - \mu_{interval})^2}}{\mu_{interval}}$ <br><br> Where $\text{interval}_i$ is a sequence of stride intervals and $u_{interval}$ is the average of all $\text{interval}_i$ |
| Band power | Average power in the input signal | bandpower = bandpower(x) <br> Where x is a matrix of the magnitude, and band power calculates the average power in each column independently |

TABLE 1-continued

| Attribute 32-1 | Attribute Description | Accelerometer Function 64 |
|---|---|---|
| Signal to noise ratio | Estimated level of noise within the data | $snr = \dfrac{power_{signal}}{power_{noise}}$ |
| Total harmonic distortion | Based upon the fundamental frequency and the first five harmonics | $thd = \dfrac{\sqrt{\sum_{i=2,3,4,5} V_i^2}}{V_1}$ Where $V_1$ is energy contained within peak of PSD at the fundamental frequency and $V_i$ is energy contained within the harmonics |

For example, during operation, assume the case where the controller 24 is configured to apply the kurtosis function as the accelerator function 64 to each segment 60-1 of the accelerometer time-series gait data 30-1. As a result of the application of the kurtosis function to the segments 60-1, the controller 24 generates kurtosis attributes 32-1-1 through 32-1-5 associated with the accelerometer time-series gait data 30-1, one attribute 32-1-1 through 32-1-5 for each segment 60-1-1 through 60-1-5. In the example provided, application of additional accelerator functions 64 (e.g., cadence function, skew function, etc.) to each segment 60-1 of the accelerometer time-series gait data 30-1 can produce five corresponding attributes (e.g., cadence attributes, skew attributes), one attribute 32-1-through 32-1-5 for each segment 60-1-1 through 60-1-5 for each accelerator function 64. In another example, during operation, the controller 24 is configured to apply all functions, such as those listed in Table 1, to each segment 60-1 of the accelerometer time-series gait data 30-1.

In another example, in the case where the time-series gait data 30 is gyroscope time-series gait data 30-2, the controller 24 is configured to apply a gyroscope function 66 to the time-series gait data 30-2 to extract a gyroscope attribute 32-2 from each of the gait data segments 60-2. In one arrangement, the gyroscope function 64 can be configured to extract an attribute 32-2 related to an XZ sway area, a YZ sway area, an XY sway area, and a sway volume associated from each of the gait data segments 60-2 associated with the gyroscope time-series gait data 30-2.

Table 2 provided below outlines four (4) attributes 32-2 that can be extracted from the gyroscope time-series gait data 30-2 by the corresponding gyroscope functions 66. It is noted that the listing of attributes 32-2 provided in Table 2 is by way of example only. It should be understood that additional attributes 32-2 can be extracted from the gyroscope time-series gait data 30-2 as well.

TABLE 2

| Attribute 32-2 | Attribute Description | Gyroscope Function 66 |
|---|---|---|
| XZ Sway Area | Area of projected gyroscope readings from Z (yaw) and X (pitch) axes | XZ Sway Area = $\pi r^2$ |
| YZ Sway Area | Area of projected gyroscope readings from Z (yaw) and axes | YZ Sway Area = $\pi r^2$ |
| XY Sway Area | Area of projected gyroscope readings from X (pitch) and Y (roll) axes | XY Sway Area = $\pi r^2$ |
| Sway Volume | Volume of projected gyroscope readings from all three axes (pitch, roll, yaw) | Sway Volume = $\dfrac{4}{3}\pi r^3$ |

Figure 4A:
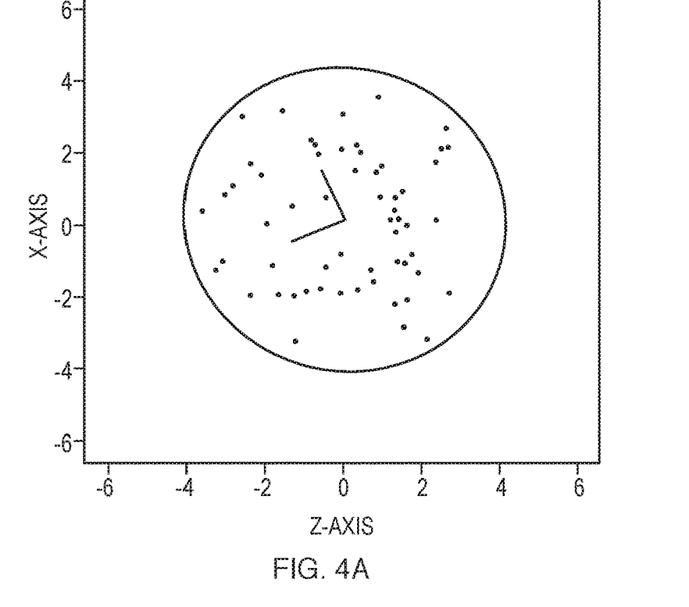
FIG. 4A illustrates an example of an XZ Sway area plot, according to one arrangement.
Figure 4B:
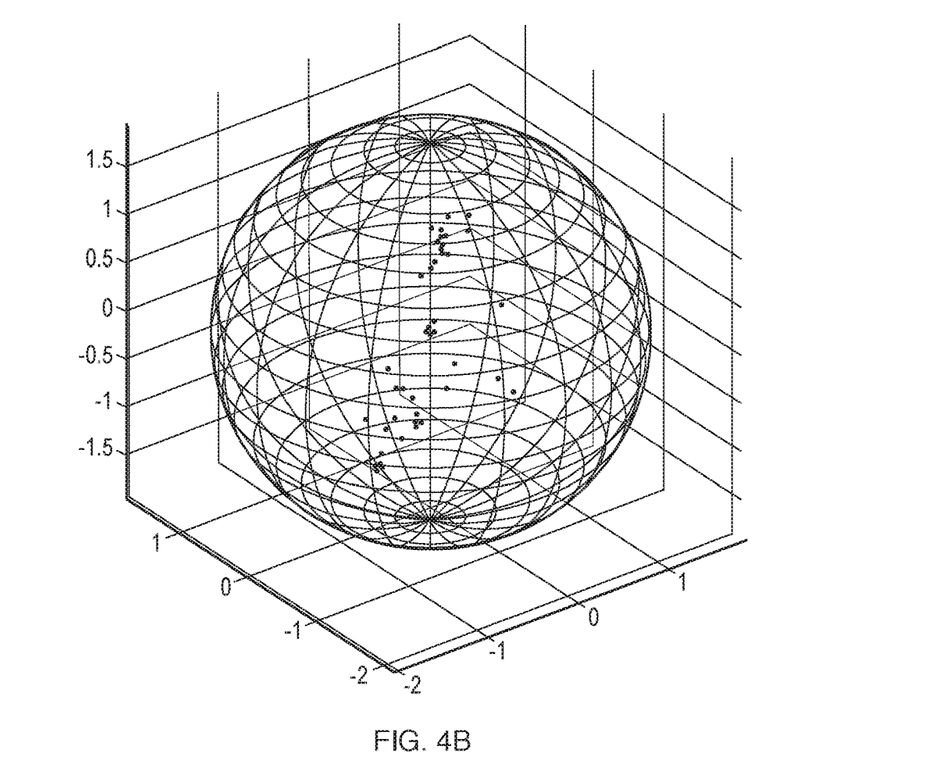
FIG. 4B illustrates an example of a sway volume plot, according to one arrangement.

During operation, the gyroscope 29 is configured to provide the rate of rotation around the X, Y and Z axes of the mobile device 20 in radians per second and the mobile sensing device 20 is configured to calculate sway area by plotting data values from two of the gyroscope's axes. For example, with reference to FIG. 4A, for a XZ sway area, the mobile sensing device 20 projects all observed gyroscope X and Z values in a segment onto an X-Z plane and provides the XZ sway area as the area of an ellipse that encloses the 95 percent confidence interval of all observed points. Further, with reference to FIG. 4B, the mobile sensing device 20 is configured to synthesize the sway volume of a user based upon the detected sway areas. In one arrangement, the mobile sensing device 20 is configured to synthesize gyroscope-based sway volume as the sphere that contains the 95 percent confidence interval of all X, Y, Z points in a given segment.

With reference to FIG. 3, assume the case where the controller 24 is configured to apply the XZ sway function as the as the gyroscope function 66 to each segment 60-2-1 through 60-2-5 of the gyroscope time-series gait data 30-2. As a result of the application of the XZ sway area function to the segments 60-2-1 through 60-2-5, the controller 24 generates XZ sway area attributes 32-2-1 through 32-2-5 associated with the gyroscope time-series gait data 30-2, one attribute 32-2-1 through 32-2-5 for each segment 60-2-1 through 60-2-5. In the example provided, application of additional gyroscope functions 64 (e.g., XY sway area function, YZ sway area function) to each segment 60-2-1 through 60-2-5 of the gyroscope time-series gait data 30-2 can generate additional corresponding attributes (e.g., XY sway area attributes, YZ sway area attributes) associated with the gyroscope time-series gait data 30-2, one attribute 32-2-1 through 32-2-5 for each segment 60-2-1 through 60-2-5. In one arrangement, during operation, the controller 24 is configured to apply all sway area functions and the sway volume function, such as those provided in Table 2, to each segment 60-1 of the accelerometer time-series gait data 30-1.

Next, with reference to FIG. 1, following generation of the attributes 32, the mobile sensing device 20 is configured to compare the set of attributes 32 with a machine learning classification model 34 previously learned from a training data set of attributes 35 to determine at least one of a blood alcohol content range of the user and an impairment level of the user.

Figure 5:
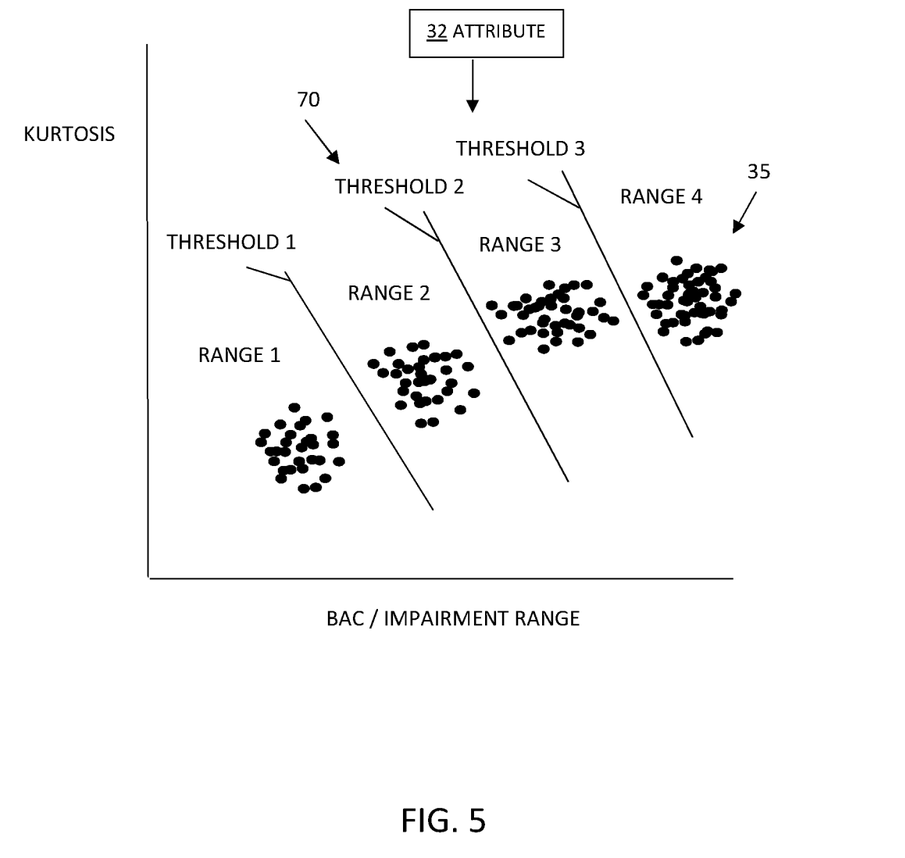
FIG. 5 illustrates an example of an application of a machine learning classification model learned from a training data set, according to one arrangement.

With reference to FIG. 5, the training data set of attributes 35 can be derived in a variety of ways. In one arrangement, the training data set of attributes 35 are derived from a test group of users. For example, the training data set of attributes 35 can be derived from a test group wearing sensor impairment goggles. The sensor impairment goggles are configured to distort the user's vision to simulate the effects of alcohol/drug consumption on the body at various BAC levels or various levels of impairment. During data collection for the training data set of attributes 35, the test group of users wear the sensor impairment goggles and walk while the accelerometer and gyroscope of the users' mobile device collect accelerometer and gyroscope sensor data. Goggles rated at various impairment levels simulate the corresponding intoxication or impairment effects. In another example, the training data set of attributes 35 can be derived from a test group where the subjects are intoxicated or impaired as a result of consuming alcohol or/and drugs.

Following the data collection, a variety of accelerometer and gyroscope attributes for each impairment level can be calculated (e.g., the accelerometer and gyroscope attributes 32-1, 32-2 provided in Tables 1 and 2 above) either on the mobile device or provided to a mobile sensing device 20, such as from a central server device. Over time, as the machine learning classification model 34 learned from the training data set of attributes 35 is updated and refined, such as with a larger population sample or with additional or fewer attributes, the server device can provide an updated machine learning classification model 34 to the mobile sensing device 20.

Based upon the groupings of each calculated accelerometer and gyroscope attributes for each impairment level determined by the test group of users, threshold values 70 between adjacent impairment levels can be calculated and provided to a mobile sensing device 20 as the machine learning classification model 34 thresholds. For example, FIG. 4 illustrates the threshold values 70 determined from the training set of kurtosis attributes 34 for four different ranges of impairment. The first range can identify a BAC of between about 0.04 and 0.06, the second range can identify a BAC of between about 0.08 and 0.15, the third range can identify a BAC of between about 0.15 and 0.25, and the fourth range can identify a BAC of between about 0.25 and 0.35.

Returning to FIG. 1, during operation, the mobile sensing device 20 is configured to compare the accelerometer attributes 32-1 and the gyroscope attributes 32-2 with the threshold values 70 learned from the training data set of attributes 35 in multi-dimensional space to determine the blood alcohol content range of the user and/or the impairment level of the user. In one arrangement, the number of dimensions associated with the comparison can relate to the number of accelerometer attributes 32-1 and the gyroscope attributes 32-2 extracted by the mobile sensing device 20. For example, as provided above, the mobile sensing device 20 is configured to extract eleven accelerometer attributes 32-1 from the accelerometer time-series gait data 30-1 and four gyroscope attributes 32-2 from the gyroscope time-series gait data 30-2. In such a case, the mobile sensing device 20 can compare all of these attributes 32-1, 32-2 with the corresponding thresholds 70 of the training data set of attributes 35 within a fifteen-dimension space to determine at least one of the blood alcohol content range of the user and the impairment level of the user for each attribute 32-1, 32-2.

With reference to FIG. 1, following the detection of one of the blood alcohol content range of the user and the impairment level of the user, the mobile sensing device 20 is configured to output a notification 36 associated with the at least one of the blood alcohol content range of the user and the impairment level of the user. For example, assume the case where the comparison of the accelerometer attributes 32-1 and the gyroscope attributes 32-2 with the threshold values 70 identifies the user as having a BAC within the range of between about 0.08 and 0.15. With such identification, the mobile sensing device 20 can generate a notification 36 identifying the user's BAC and provide the notification 36 to a display 28 associated with the mobile sensing device 20. In another example, the mobile sensing device 20 can generate the notification 36 and forward it to an external device, such as the device of a person identified in the mobile sensing device's contact list or to a taxi or third-party driving service.

Accordingly, the mobile sensing device 20 is configured to utilize accelerometer time-series gait data 30-1 and gyroscope time-series gait data 30-2, as well as posturography features, including sway area and sway volume computed on the accelerometer and gyroscope time-series gait data 30-1, 30-2, to classify a user's BAC range or level of impairment. Based upon this configuration, the mobile sensing device 20 can provide timely notifications of excessive alcohol consumption to drinkers who are over the legal driving limit. Also, the mobile sensing device 20 can log a user's drinking patterns and associated contexts (e.g., time, place, or who with) such that the user can reflect on his drinking logs, detect patterns of abuse, and either self-correct or seek treatment. The mobile sensing device 20 can also provide notifications to smartphone users whose gait have been impaired for other reasons including illicit or prescription drug use, fatigue or adverse health conditions.

Further, the mobile sensing device 20 is configured to operate passively to determine the user's level of intoxication or impairment. By limiting the need for active user engagement, the mobile sensing device 20 can be readily adopted and scaled. Additionally, the detection application is configured to be executed by a user's mobile sensing device 20, such as a smartphone or smartwatch. As such, the user is not required to purchase a dedicated, stand-alone device to monitor his BAC range or impairment levels.

As provided above, the mobile sensing device 20 is configured to detect a set of attributes 32 associated with time-series gait data 30 and to compare the set of attributes 32 with a machine learning classification model 34 learned from a training data set of attributes 35 to determine at least one of a blood alcohol content range of the user and an impairment level of the user. In one arrangement, the mobile sensing device 20 is configured to modify at least some of the set of attributes 32 prior to comparing with the machine learning classification model 34 to provide a more robust and accurate comparison results relative to the a machine learning classification model 34.

Figure 6:
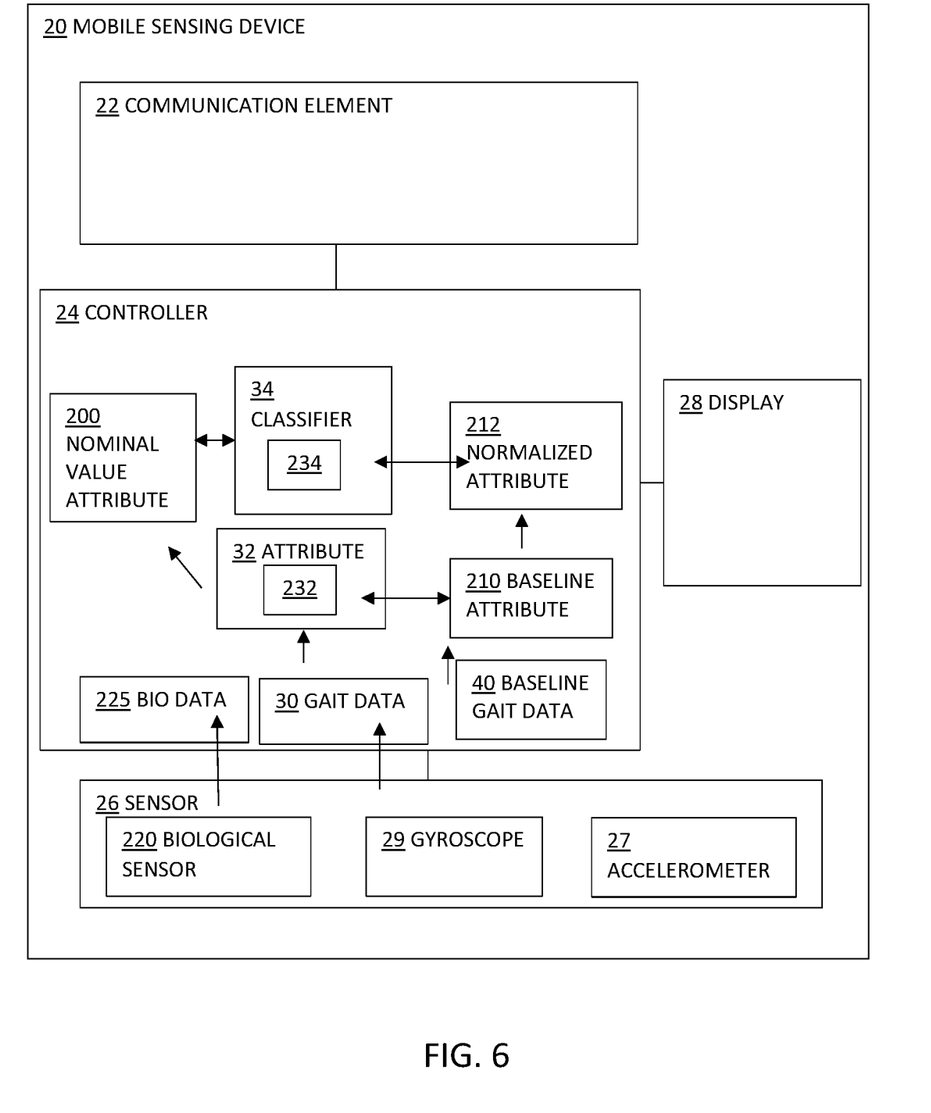
FIG. 6 illustrates a schematic representation of a mobile sensing device, according to one arrangement.
Figure 7:
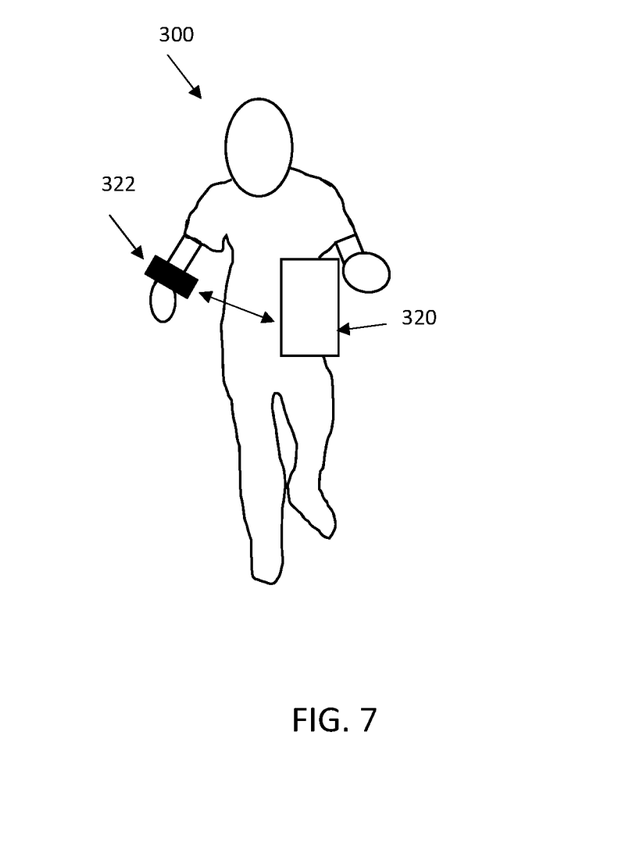
FIG. 7 illustrates a schematic diagram of a user utilizing both a first and second mobile device to detect a blood alcohol content level or impairment level, according to one arrangement.

For example, with reference to FIG. 6, after detecting the set of attributes 32 associated with the collected time-series gait data 30 the mobile sensing device 20 is configured to detect an nominal value of each attribute of the set of attributes 200 associated with the time-series gait data 30. For example, the mobile sensing device 20 can apply a nominal value function to each segment 60 of the attributes 32 extracted from either the accelerometer time-series gait data 30-1 or the gyroscope time-series gait data 30-2 to generate nominal value attributes 200. With such application of the nominal value function, the mobile sensing device 20 can effectively classify the value generated by the attribute function. The mobile sensing device 20 can then compare the nominal value of each attribute of the set of attributes 200 with machine learning classification model thresholds 70 to determine the at least one of the blood alcohol content range of the user and the impairment level of the user.

In one arrangement, to compensate for differences in walking patterns of different people, the mobile sensing device 20 can be configured to normalize the attributes 32 extracted from the time-series gait data 30. For example, assume the case where a user has a relatively large XZ sway area as he walks under sober circumstances but which would be indicative of the user having a relatively high impairment level. To minimize the effect of such differences in gait patterns on a user's detected BAC or impairment level, the mobile sensing device 20 can be configured to utilize the baseline gait data 40 to normalize the attributes 32.

For example, with continued reference to FIG. 6, the mobile sensing device 20 is configured to combine each attribute of the set of attributes 32 and a corresponding baseline attribute 210 associated with baseline time-series gait data 40 to generate a set of normalized attributes 212 independent from a baseline motion of the user. The mobile sensing device 20 can combine the attributes 32 and the baseline attribute 210 to generate the normalized attributes 212 in a variety of ways. In one example, the mobile sensing device 20 can generate the normalized attributes 212 as a ratio between each attribute 32 and each corresponding baseline attribute 210. In another example, the mobile sensing device 20 can generate the normalized attributes 212 as a difference between each attribute 32 and each corresponding baseline attribute 210. Such a combination normalizes the attributes 32 of a set of time-series gait data 30 to minimize or remove anomalies in a particular user's walking pattern (e.g., a relatively large XZ sway area) when comparing each attribute of the set of normalized attributes with the machine learning classification model 34 to determine the at least one of the blood alcohol content range of the user and the impairment level of the user. While the mobile sensing device 20 can generate the normalized attributes 212 as a ratio or difference, the mobile sensing device 20 can be configured to generate the normalized attributes 212 using a variety of other operations as well.

As indicated in the example above, the mobile device 20 is configured to compare each of the eleven accelerometer attributes 32-1 and each of the four gyroscope attributes 32-2 with corresponding attributes of the machine learning classification model 34 to determine either a BAC range or an impairment level of the user. Such indication is by way of example only. In one arrangement, and with continued reference to FIG. 6, the machine learning classification model 34 is configured with a pre-selected subset of classification attributes 234 which have a relatively high predictive values for BAC or impairment classification.

For example, to quantify the predictive value of each extracted attribute 32, the machine learning classification model 34 can be developed using a Correlation-Based Feature Selection (CFS). Here, each attribute's correlation with a test subject's BAC level and p-value are computed. Attributes that have statistically significant correlations (p-value<0.05) with BAC levels have a relatively high predictive value and are included as part of the machine learning classification model 34.

In one arrangement, assume the case where of the pre-selected machine learning classification model attributes 234 includes the attributes of cadence, symmetry of a walking pattern, and kurtosis. During operation, upon review of the pre-selected machine learning classification model attributes 234, the mobile sensing device 20 is configured to select the corresponding attributes 232 from the entire set of eleven attributes extracted from the time-series gait data 30 and to compare these selected attributes 232 with the corresponding pre-selected attributes 234 of the machine learning classification model attributes 234. Such a comparison utilizes the machine learning classification model attributes 234 that provide the relatively highest predictive value for BAC or impairment classification. In one arrangement, CFS can be performed offline, wherein the most predictive features are pre-determined during analysis and used to generate the BAC or impairment classification model utilized on the mobile sensing device 20.

As provided above, the mobile sensing device 20 is configured to utilize sensors, such as an accelerometer 27 and a gyroscope 29 to generate time-series gait data 30 for analysis. In one arrangement, the mobile sensing device 20 can utilize other sensors as well. For example, with reference to FIG. 6, the mobile sensing device 20 can include a biological sensor 220 configured to provide time-series biological data 225 to the controller 24 as a user walks. The biological sensor 220 can be configured to provide any of a variety of biological data 225 to the controller 24, such as heart rate, heart rate variability, skin temperature, galvanic skin resistance, respiration, temperature, and perspiration information for example. Upon receipt, the mobile sensing device is configured to detect a set of attributes associated with the second time-series biological data 25 and to compare the extracted attributes with the machine learning classification model 34 to determine the user's BAC or impairment level.

As provided above, the mobile sensing device 20 is configured to operate passively to determine the user's level of intoxication or impairment, which limits the need for active user engagement during operation. Such configuration is by way of example only. In one arrangement, the mobile sensing device 20 is configured to operate the application actively. For example, the application can be activated on a mobile sensing device 20 by a law enforcement officer to test a suspect for DUI. In use, the officer can activate the application on his own mobile sensing device 20, hand the mobile sensing device 20 to the suspect, and asks the suspect to walk. With such a configuration, the mobile sensing device 20 can provide an accurate assessment of the suspect's BAC or impairment level without requiring the use of a breathalyzer.

As indicated above, the mobile sensing device 20 is configured as a single device, such as a mobile phone (e.g., smartphone), mobile watch (e.g., smartwatch), a tablet device, a laptop computer, or other computerized device. Such indication is by way of example only. In one arrangement, the functionality of the mobile sensing device 20 can be divided across multiple devices. For example, with reference to FIG. 6, a user 300 can utilize multiple mobile sensing devices such as a smartphone 320 and a smartwatch 322 to collect time-series gait data 30.

In one arrangement, the smartphone 320 is typically carried on the body of the user, such as in a pocket, and can collect substantially accurate cadence and sway data attributes as part of the time-series gait data 30, associated with the user. The smartwatch 322 is configured as a wearable device and can collect both various attributes including cadence and sway data attributes from the user as part of the time-series gait data 30 as well as physiologic or biological data 225 from the user.

The use of both the smartphone 320 and a smartwatch 322 allows collaborative data collection during walking. For example, when a user wears both devices 320, 322, gyroscope and accelerometer data can be collected on both the smartwatch 322 and smartphone 322. The smartwatch time-series gait data 30 is then sent to the smartphone 320 where it is segmented along with the smartphone's sensor data, such as into 5 second segments. The mobile sensing device 20 extracts the attributes 32 from the time-series gait data 30, compares to the machine learning classification model 34, and provides the resulting, inferred BAC range or impairment level as a notification 36, such as to the smartwatch 322 where it is displayed.

As provided above, the mobile sensing device 20 is described as extracting attributes 32 from time-series gait data 30. Such description is by way of example only. In one arrangement, attribute extraction can be computationally intense. Accordingly, following segmentation, the mobile sensing device 20 is configured to transmit the segmented time-series gait data 30 to a sever device (not shown) which, in turn, is configured to extract the attributes 32 from the time-series gait data 30.

While various embodiments of the innovation have been particularly shown and described, it will be understood by those skilled in the art that various changes in form and details may be made therein without departing from the spirit and scope of the innovation as defined by the appended claims.

What is claimed is:

1. In a mobile sensing device, a method of detecting blood alcohol content, comprising:
receiving, by the mobile sensing device, time-series gait data from at least one sensor of the mobile sensing device as a user walks;
detecting, by the mobile sensing device, a set of attributes associated with the time-series gait data, each attribute of the set of attributes related to the user's gait;
comparing, by the mobile sensing device, the set of attributes with a machine learning classification model learned from a training data set of attributes to determine at least one of a blood alcohol content range of the user and an impairment level of the user; and
outputting, by the mobile sensing device, a notification associated with the at least one of the blood alcohol content range of the user and the impairment level of the user;
wherein comparing the set of attributes with the machine learning classification model comprises:
combining, by the mobile sensing device, each attribute of the set of attributes and a corresponding baseline attribute associated with baseline time-series gait data to generate a set of normalized attributes independent from a baseline motion of the user, and
comparing, by the mobile sensing device, each attribute of the set of normalized attributes with the machine learning classification model to determine the at least one of the blood alcohol content range of the user and the impairment level of the user.

2. The method of claim 1, wherein:
receiving the time-series gait data from the at least one sensor of the mobile sensing device as the user walks further comprises receiving, by the mobile sensing device, time-series biological data from at least one biological sensor of the mobile sensing device as a user walks; and
detecting the set of attributes associated with the time-series gait data comprises detecting, by the mobile sensing device, a set of attributes associated with the time-series biological data, each attribute of the set of attributes related to the user's gait.

3. The method of claim 1, wherein receiving time-series gait data from the at least one sensor of the mobile sensing device comprises:
receiving, by the mobile sensing device, a user motion signal from the at least one sensor of the mobile sensing device;
comparing, by the mobile sensing device, the user motion signal with a walking signature signal; and
when the user motion signal substantially corresponds to the walking signature signal receiving, by the mobile sensing device, time-series gait data from the at least one sensor of the mobile sensing device as the user walks.

4. The method of claim 1, comprising:
in response to receiving the time-series gait data, dividing, by the mobile sensing device, the time-series gait data into gait data segments; and
detecting the set of attributes associated with the time-series gait data comprises detecting, by the mobile sensing device, a set of attributes associated with each gait data segment of the time-series gait data.

5. The method of claim 4, comprising, in response to dividing the time-series gait data into gait data segments:
identifying, by the mobile sensing device, at least one outlier value of the time-series gait data; and
removing, by the mobile sensing device, the at least one outlier value from the time-series gait data prior to detecting the set of attributes.

6. The method of claim 1, wherein receiving time-series gait data from at least one sensor comprises receiving, by the mobile sensing device, time-series gait data from an accelerometer and from a gyroscope of the mobile sensing device.

7. The method of claim 6, wherein detecting the set of attributes associated with the time-series gait data comprises detecting, by the mobile sensing device, a set of accelerometer attributes associated with the time-series gait data, the set of accelerometer attributes selected from the group consisting of a number of steps taken, cadence, symmetry of walking pattern, kurtosis, average gait velocity, residual step length, harmonic ratio of high and low frequencies, residual step time, bandpower, signal to noise ratio, and total harmonic distortion.

8. The method of claim 6, wherein detecting the set of attributes associated with the time-series gait data comprises detecting, by the mobile sensing device, a set of gyroscope attributes associated with the time-series gait data, the set of gyroscope attributes selected from the group consisting of an XZ sway area, a YZ sway area, an XY sway area, and a sway volume.

9. A mobile sensing device, comprising:
at least one sensor; and
a controller having a processor and a memory, the controller disposed in electrical communication with the at least one sensor, the controller configured to:
receive time-series gait data from at least one sensor of the mobile sensing device as a user walks;
detect a set of attributes associated with the time-series gait data, each attribute of the set of attributes related to the user's gait;
compare the set of attributes with a machine learning classification model learned from a training data set of attributes to determine at least one of a blood alcohol content range of the user and an impairment level of the user; and
output a notification associated with the at least one of the blood alcohol content range of the user and the impairment level of the user;
wherein when comparing the set of attributes with the machine learning classification model, the controller is configured to:
combine each attribute of the set of attributes and a corresponding baseline attribute associated with baseline time-series gait data to generate a set of normalized attributes independent from a baseline motion of the user, and compare each attribute of the set of normalized attributes with the machine learning classification model to determine the at least one of the blood alcohol content range of the user and the impairment level of the user.

10. The mobile sensing device of claim 9, wherein:

when receiving the time-series gait data from the at least one sensor of the mobile sensing device as the user walks further, the controller is configured to receive time-series biological data from at least one biological sensor of the mobile sensing device as a user walks; and when detecting the set of attributes associated with the time-series gait data, the controller is configured to detect a set of attributes associated the time-series biological data, each attribute of the set of attributes related to the user's gait.

11. The mobile sensing device of claim 9, wherein when receiving time-series gait data from the at least one sensor of the mobile sensing device, the controller is configured to:

receive a user motion signal from the at least one sensor of the mobile sensing device;

compare the user motion signal with a walking signature signal; and when the user motion signal substantially corresponds to the walking signature signal receive time-series gait data from the at least one sensor of the mobile sensing device as the user walks.

12. The mobile sensing device of claim 9, wherein the controller is configured to:

in response to receiving the time-series gait data, divide the time-series gait data into gait data segments; and when detecting the set of attributes associated with the time-series gait data, detect a set of attributes associated with each gait data segment of the time-series gait data.

13. The mobile sensing device of claim 12 wherein, when dividing the time-series gait data into gait data segments, the controller is configured to:

identify at least one outlier value of the time-series gait data; and remove the at least one outlier value from the time-series gait data prior to detecting the set of attributes.

14. The mobile sensing device of claim 9, wherein when receiving time-series gait data from at least one sensor, the controller is configured to receive time-series gait data from an accelerometer and from a gyroscope of the mobile sensing device.

15. The mobile sensing device of claim 14, wherein when detecting the set of attributes associated with the time-series gait data, the controller is configured to detect a set of accelerometer attributes associated with the time-series gait data, the set of accelerometer attributes selected from the group consisting of a number of steps taken, cadence, symmetry of walking pattern, kurtosis, average gait velocity, residual step length, harmonic ratio of high and low frequencies, residual step time, bandpower, signal to noise ratio, and total harmonic distortion.

16. The mobile sensing device of claim 14, wherein when detecting the set of attributes associated with the time-series gait data, the controller is configured to detect a set of gyroscope attributes associated with the time-series gait data, the set of gyroscope attributes selected from the group consisting of an XZ sway area, a YZ sway area, an XY sway area, and a sway volume.

17. A computer program product stored on a computer readable medium that when executed by a controller of a mobile sensing device configured the mobile sensing device to:

receive time-series gait data from at least one sensor of the mobile sensing device as a user walks;

detect a set of attributes associated with the time-series gait data, each attribute of the set of attributes related to the user's gait;

combine each attribute of the set of attributes and a corresponding baseline attribute associated with baseline time-series gait data to generate a set of normalized attributes independent from a baseline motion of the user; and compare each attribute of the set of normalized attributes with a machine learning classification model learned from a training data set of attributes to determine at least one of a blood alcohol content range of the user and an impairment level of the user; and output a notification associated with the at least one of the blood alcohol content range of the user and the impairment level of the user.

* * * * *